United States Patent
Onvlee et al.

(10) Patent No.: US 7,283,225 B2
(45) Date of Patent: Oct. 16, 2007

(54) PARTICLE DETECTION DEVICE, LITHOGRAPHIC APPARATUS AND DEVICE MANUFACTURING METHOD

(75) Inventors: Johannes Onvlee, s-Hertogenbosch (NL); Raimond Visser, Best (NL); Peter Ferdinand Greve, Eindhoven (NL); Johannes Hendrikus Gertrudis Franssen, Eersel (NL); Erwin Theodorus Jacoba Verhagen, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 11/242,146

(22) Filed: Oct. 4, 2005

(65) Prior Publication Data

US 2006/0072108 A1 Apr. 6, 2006

Related U.S. Application Data

(63) Continuation of application No. 10/957,752, filed on Oct. 5, 2004.

(51) Int. Cl.
*G01N 21/00* (2006.01)
(52) U.S. Cl. .................................. 356/237.2; 356/237.5
(58) Field of Classification Search ...................... None
See application file for complete search history.

(56) References Cited

U.S. PATENT DOCUMENTS 5,745,236 A * 4/1998 Haga .......................... 356/600
6,222,624 B1 * 4/2001 Yonezawa ................ 356/237.1

* cited by examiner

*Primary Examiner*—Michael P. Stafira
(74) *Attorney, Agent, or Firm*—Pillsbury Winthrop Shaw Pittman LLP

(57) ABSTRACT

To enable differentiation between a particle and a ghost particle, a detector system resolves radiation from a ghost particle from radiation from an actual particle. The detector system outputs at least two detector signals corresponding to intensities of radiation being incident on different parts of the detector system or the detector system outputs at least two detector signals corresponding to intensities of radiation with different wavelengths being incident on the detector system. If radiation is received from a ghost particle, not each of the at least two detector signals has a level above a predetermined threshold level, whereas radiation received from a particle results in the signals having substantially a same level above a threshold level. The detector system may include a radiation detector device configured to generate the first detector signal in response to radiation incident on at least one predetermined part of the radiation detector device and a radiation blocking assembly configured to prevent radiation not originating from a particle from being incident on the predetermined part of the detector device.

35 Claims, 5 Drawing Sheets

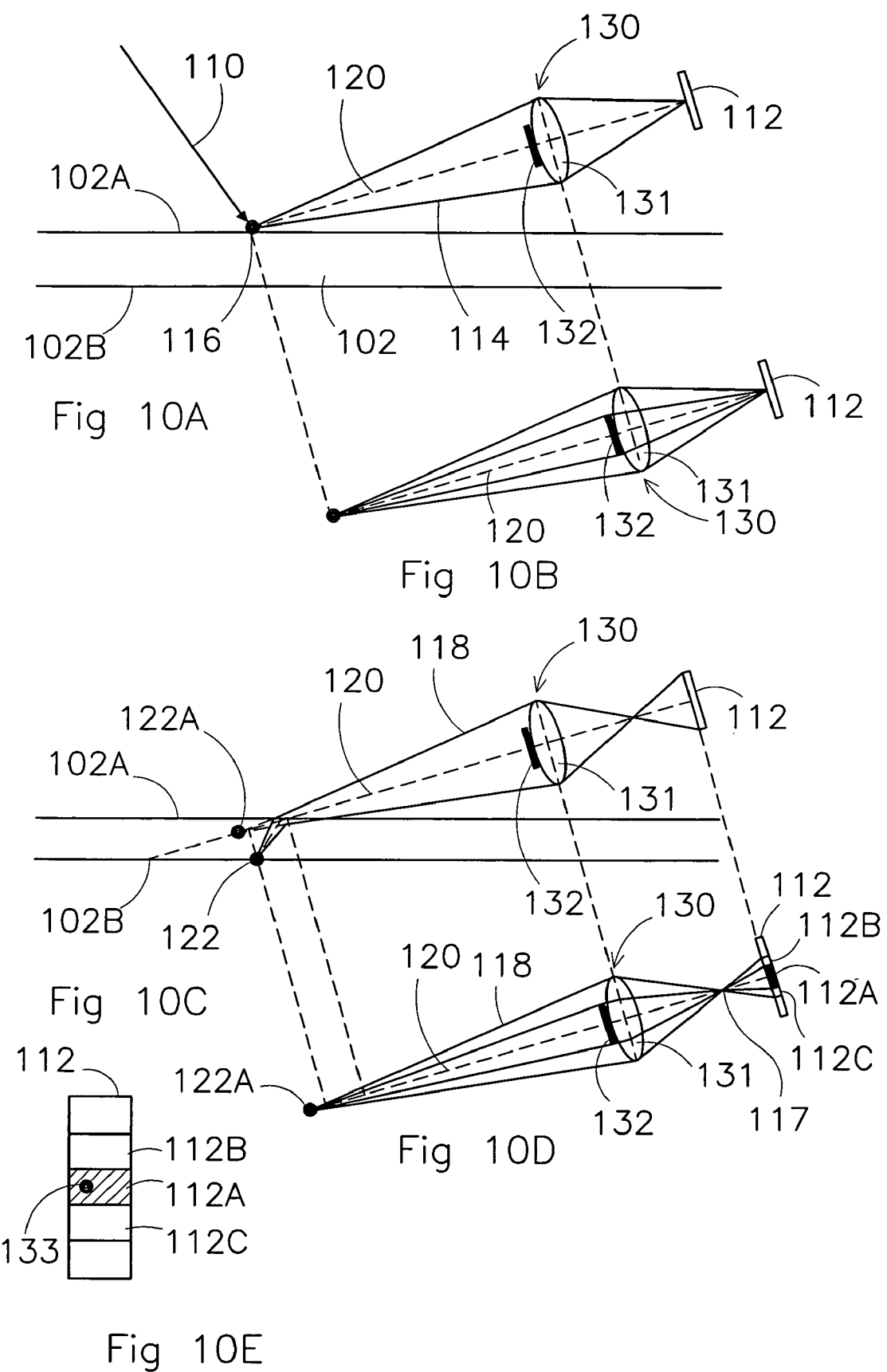

PARTICLE DETECTION DEVICE, LITHOGRAPHIC APPARATUS AND DEVICE MANUFACTURING METHOD

CROSS REFERENCE TO RELATED APPLICATION

This application is a continuation of U.S. application Ser. No. 10/957,752, filed Oct. 5, 2004, the entire contents of which are hereby incorporated by reference.

BACKGROUND OF THE INVENTION

1. Field of the Invention

The present invention relates to a particle detection device, a lithographic apparatus including a particle detection device and a device manufacturing method.

2. Description of the Related Art

A lithographic apparatus is a machine that applies a desired pattern onto a target portion of a substrate. Lithographic apparatus can be used, for example, in the manufacture of integrated circuits (ICs). In that circumstance, a patterning device, such as a mask, may be used to generate a circuit pattern corresponding to an individual layer of the IC, and this pattern can be imaged onto a target portion (e.g. including part of, one, or several dies) on a substrate (e.g. a silicon wafer) that has a layer of radiation-sensitive material (resist). In general, a single substrate will contain a network of adjacent target portions that are successively exposed. Conventional lithographic apparatus include so-called steppers, in which each target portion is irradiated by exposing an entire pattern onto the target portion at once, and so-called scanners, in which each target portion is irradiated by scanning the pattern through the projection beam in a given direction (the "scanning"-direction) while synchronously scanning the substrate parallel or anti-parallel to this direction.

The imaging of the pattern including small structures, possibly protected by a pellicle, is very sensitive to dust and other contamination of the patterning device and substrate. Therefore, before imaging, the patterning device (and/or the pellicle protecting the small structures thereof) and substrate are tested for contamination, in particular for particles. In conventional lithographic apparatus, a particle detection system directs a beam of radiation, in particular (but not necessarily) monochrome radiation, i.e. radiation having substantially one wavelength, on a surface of an object, for example, but not limited to, the patterning device or the substrate. The object and/or the beam move in order to scan the surface of the object. When the beam of radiation engages the surface of the object, the radiation is partially reflected according to physical laws of reflection (an exit angle is identical to an angle of incidence with respect to a fictitious line perpendicular to the surface (the normal)). Another part of the incident radiation may enter the object, such as the patterning device or substrate, and is refracted. In both cases, the beam is anisotropically redirected. When the beam of radiation engages a contaminating particle, the radiation is scattered, i.e. reflected isotropically.

A radiation detector is positioned with respect to the surface and the beam of radiation such that radiation reflected on the surface is not incident on the detector, but a part of the radiation scattered, i.e. being reflected in substantially every direction, by a particle or other contamination is incident on the detector. Thus, the detector receives radiation only when the beam of radiation is scattered by a particle or other contamination.

A part of the radiation incident on the surface of the object enters the object and is refracted, as above mentioned. Inside the object, the beam may be refracted and/or diffracted by the chrome pattern and/or reflected one or more times. Depending on a number of parameters, such as the material, the size, the geometry, and the like, a part of the radiation that entered the object will leave the object again in the direction of the detector. In that case, the detector detects radiation not being scattered by a particle. As a result a detection circuit receiving a signal from the detector determines that a particle is present, although no particle is actually present. Such a detected, but not actually present particle will hereinafter be referred to as a ghost particle.

In other conventional systems for detecting particles, a microscope may be used. Such systems use a microscope to scan the surface and may perform a detailed analysis of any detected particle. However, such systems are expensive and less suitable for mere in-line detection of particles.

SUMMARY OF THE INVENTION

Embodiments of the invention include a simple and cost-effective particle detection system for in-line detection of particles on a surface of an object, which system is capable of discriminating between a signal from a particle and an erroneous signal, i.e. a ghost particle signal. Radiation from a ghost particle may be spatially, or otherwise, resolved from radiation from an actual particle.

According to an embodiment of the invention, there is provided a particle detection system configured to detect a particle on a surface of an object, the system including a first radiation source configured to generate a beam of radiation having a first wavelength, the beam being directed at a detection area at the surface of the object; a radiation detector system configured to output at least two detector signals corresponding to an intensity of radiation received from the detection area being incident on the detector system; a detection circuit configured to determine from the at least two detector signals whether a particle is present on the surface of the object; wherein the detection circuit is configured to compare the at least two detector signals with a predetermined threshold level, and to indicate that a particle is present on the surface of the object, when each of the at least two detector signals has a level above the threshold level.

The particle detection system according to embodiments of the present invention is capable of discriminating between isotropic and non-isotropic radiation. As mentioned above, radiation scattered by a particle is isotropic radiation. Radiation coming from the radiation source and being refracted, reflected and diffracted internally of the object and thereafter being incident on the detector system is anisotropic as will be explained below in relation to the drawings.

Starting with a beam of light directed at a detection area at the surface of the object, isotropicly redirected radiation may be distinguished from anisotropicly redirected, i.e. scattered, radiation, since anisotropic radiation has a predetermined cross-section, i.e. a limited cross-section, for example a circle, rectangle or any other shape. Such a limited beam results in a corresponding limited spot, when incident on a surface, such as the surface of a detector or any other surface in the trajectory of the beam of radiation. Isotropicly scattered radiation, on the contrary, does not result in such a limited spot. Isotropicly scattered radiation is directed in virtually any direction. Thus, the isotropic part of the radiation incident on the detector system may be distinguished from an anisotropic part by evaluating whether any concentrated light spot is present in the beam of radiation. The discrimination based on the distribution and location of radiation on a surface of the detector system will hereinafter be referred to as spatial discrimination.

The radiation incident on the detector system may be detected such, that at least two signals are generated, for example using more than one signal from one detector or one signal from each of more detectors, from which it may be deduced whether the incident radiation includes isotropicly redirected and/or anisotropically redirected radiation. Generating at least two signals from the radiation on the detector system is performed such that spatial information may be derived from the combination of the at least two signals. A detection circuit may determine whether the incident radiation originates from a particle or from a ghost particle by e.g. spatially resolving radiation from a ghost particle and radiation from an actual particle.

A cross-sectional shape of the beam of radiation coming from the radiation source may be round (a circle) or may have any other shape, a line for example. The radiation having a first wavelength may be monochrome radiation, but may also include radiation having a wavelength in a certain range. In particular, when only one radiation source is used, even white light, i.e. radiation including many wavelengths in the visible range, may be used.

The radiation detector system may include a simple radiation sensitive device or it may be a one or two-dimensional radiation-sensitive device such as a 1D (linear) or 2D (planar) CCD-element or one or two-dimensional radiation-sensitive photo diode (PSD).

The particle detection system may be configured to determine a size of a detected particle based on the detector signals. As mentioned above, the detector system may comprise a detector device comprising an array of detector pixel elements (e.g. a 2D (planar) CCD-element), each detector signal of the plurality of detector signals corresponding to an intensity of radiation incident on at least one detector pixel element, thereby providing a particle image of a detected particle, the image comprising an array of image pixels, wherein the detection circuit is configured to: detect whether a detected particle is small or large based on the particle image; determine the size of a small particle based on the radiation intensity incident on at least one detector pixel element; and determine the size of a large particle based on image features of the particle image.

According to an embodiment of the invention, there is provided a lithographic apparatus including an illumination system configured to condition a beam of radiation; a support structure configured to support a patterning device, the patterning device serving to impart the beam of radiation with a pattern in its cross-section; a substrate table configured to hold a substrate; a particle detection system configured to verify that substantially no particles are present on a surface of the patterning device or the substrate; and a projection system configured to project the patterned beam onto a target portion of the substrate, wherein the particle detection system includes a detection circuit, which is configured to compare at least two detector signals with a predetermined threshold level, and to indicate that a particle is present on the surface of the object, when each of the at least two detector signals has a level above the threshold level.

According to a further embodiment of the invention, there is provided a device manufacturing method including providing a substrate; providing a beam of radiation using an illumination system; using a patterning device to impart the projection beam with a pattern in its cross-section; projecting the patterned beam of radiation onto a target portion of the substrate; and verifying that substantially no particles are present on a surface of the patterning device or the substrate using a particle detection system, wherein the particle detection system includes a detection circuit, which is configured to compare at least two detector signals with a predetermined threshold level, and to indicate that a particle is present on the surface of the object, when each of the at least two detector signals has a level above the threshold level.

A device manufacturing method including projecting a patterned beam of radiation onto a target portion of a substrate; and detecting a particle on a surface of an object, the detecting including providing a beam of radiation directed at a detection area at the surface of the object, detecting the beam of radiation scattered by a particle; outputting a plurality of signals corresponding to an intensity of the detected beam of radiation, and comparing the plurality of signals with a predetermined threshold level to determine whether a particle is present on the surface of the object.

A particle detection system configured to detect a particle on a surface of an object, in accordance with an embodiment of the invention includes a first radiation source configured to generate a beam of radiation having a first wavelength, the beam of radiation being directed to the surface of the object; a radiation detector system configured to output a plurality of detector signals corresponding to an intensity of radiation incident on the detector system; and a detection circuit coupled to the radiation detector system and configured to determine from the plurality of detector signals whether a particle is present on the surface of the object; wherein the detection circuit is configured to compare the plurality of detector signals with a predetermined threshold level, and to indicate that a particle is present on the surface of the object, when the plurality of detector signals has a level above the threshold level.

A particle detection system configured to detect a particle on a surface of an object, in accordance with an embodiment of the invention comprises a radiation source configured to generate a beam of radiation, the beam of radiation being directed to the surface of the object; a radiation detector system configured to output at least a first detector signal corresponding to an intensity of radiation incident on the detector system; and a detection circuit coupled to the radiation detector system and configured to determine from the at least one detector signal whether a particle is present on the surface of the object. The radiation detector system comprises a radiation detector device for generating the first detector signal in response to radiation incident on at least one predetermined part of the radiation detector device; and a radiation blocking assembly for preventing radiation not originating from within a detection range around the surface of the object from being incident on the predetermined part of the detector device. Thus, the radiation from a ghost particle and radiation from an actual particle is spatially resolved in a plane of the detector of the detector system. As a result, the detector signal is only dependent on radiation originating from scattering by a particle on the surface of the object.

In the above embodiment, the radiation detector system may be configured to further output at least a second detector signal for indicating whether radiation is incident on the detector device outside said at least one predetermined part of the detector device. Thus, a second signal may be indicative for the presence of radiation originating from a ghost particle.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist) or a metrology or inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

The terms "radiation" and "beam" used herein encompass all types of electromagnetic radiation, including ultraviolet (UV) radiation (e.g. having a wavelength of 365, 248, 193, 157 or 126 nm) and extreme ultra-violet (EUV) radiation (e.g. having a wavelength in the range of 5-20 nm), as well as particle beams, such as ion beams or electron beams.

The term "patterning device" used herein should be broadly interpreted as referring to a device that can be used to impart a beam of radiation with a pattern in its cross-section such as to create a pattern in a target portion of the substrate. It should be noted that the pattern imparted to the beam of radiation may not exactly correspond to the desired pattern in the target portion of the substrate. Generally, the pattern imparted to the beam of radiation will correspond to a particular functional layer in a device being created in the target portion, such as an integrated circuit.

Patterning devices may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions; in this manner, the reflected beam is patterned. In each example of patterning device, the support structure may be a frame or table, for example, which may be fixed or movable as required and which may ensure that the patterning device is at a desired position, for example with respect to the projection system. Any use of the terms "mask" or "mask" herein may be considered synonymous with the more general term "patterning device".

The term "projection system" used herein should be broadly interpreted as encompassing various types of projection system, including refractive optical systems, reflective optical systems, and catadioptric optical systems, as appropriate for example for the exposure radiation being used, or for other factors such as the use of an immersion fluid or the use of a vacuum. Any use of the term "lens" herein may be considered as synonymous with the more general term "projection system".

The illumination system may also encompass various types of optical components, including refractive, reflective, and catadioptric optical components for directing, shaping, or controlling the projection beam of radiation, and such components may also be referred to below, collectively or singularly, as a "lens".

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein the substrate is immersed in a liquid having a relatively high refractive index, e.g. water, so as to fill a space between the final element of the projection system and the substrate. Immersion liquids may also be applied to other spaces in the lithographic apparatus, for example, between the mask and the first element of the projection system. Immersion techniques are well known in the art for increasing the numerical aperture of projection systems.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIGS. 10A and 10C are a schematical side view of an embodiment of a particle detection system having a radiation blocking assembly;

FIGS. 10B and 10D are a schematical top view of the embodiment of FIGS. 10A and 10C, respectively; and FIG. 10E schematically shows a detector plane of a detector device of the embodiment of FIGS. 10A-10D.

DETAILED DESCRIPTION OF THE INVENTION

Figure 1:
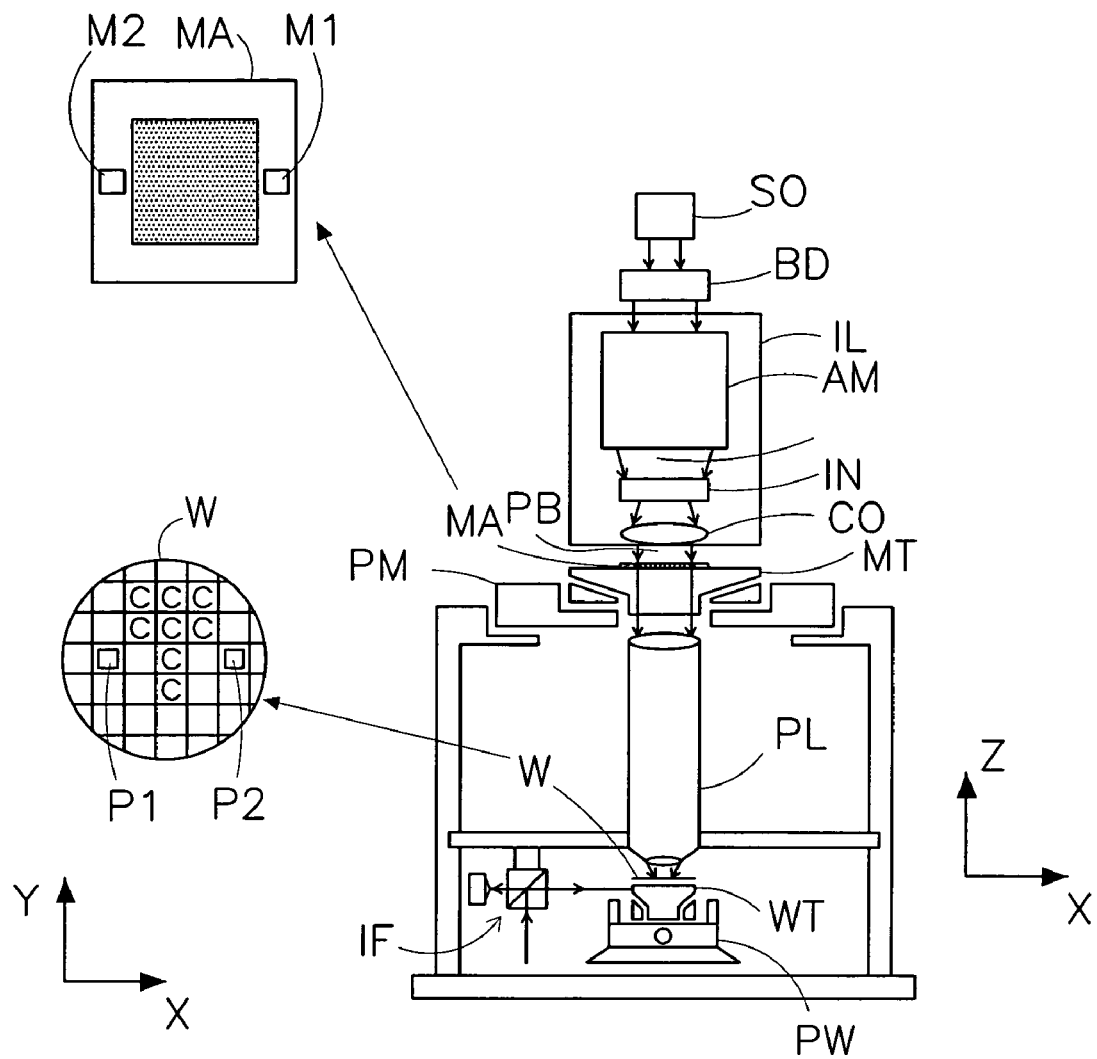
FIG. 1 depicts a lithographic apparatus according to an embodiment of the invention.

FIG. 1 schematically depicts a lithographic apparatus according to an embodiment of the invention. The apparatus includes an illumination system (illuminator) IL configured to provide a beam PB of radiation (e.g. UV radiation), and a first support structure (e.g. a mask table) MT configured to support a patterning device (e.g. a mask) MA and connected to a first positioning device PM configured to accurately position the patterning device with respect to the projection system, item PL ("lens"). The apparatus also includes a substrate table (e.g. a wafer table) WT configured to hold a substrate (e.g. a resist-coated wafer) W and connected to a second positioning device PW configured to accurately position the substrate with respect to the projection system, item PL ("lens"); the projection system (e.g. a refractive projection lens) PL being configured to image a pattern imparted to the beam of radiation PB by the patterning device MA onto a target portion C (e.g. including one or more dies) of the substrate W.

As here depicted, the apparatus is of a transmissive type (e.g. employing a transmissive mask). Alternatively, the apparatus may be of a reflective type (e.g. employing a programmable mirror array of a type as referred to above).

The illuminator IL receives a beam of radiation from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including for example suitable directing mirrors and/or a beam expander. In other cases, the source may be integral part of the apparatus, for example, when the source is a mercury lamp. The source SO and the illuminator IL, together with the beam delivery system BD if required, may be referred to as a radiation system.

The illuminator IL may include an adjusting device AM configured to adjust the angular intensity distribution of the beam. Generally, at least the outer and/or inner radial extent (commonly referred to as σ-outer and σ-inner, respectively) of the intensity distribution in a pupil plane of the illuminator can be adjusted. In addition, the illuminator IL generally includes various other components, such as an integrator IN and a condenser CO. The illuminator provides a conditioned beam of radiation, referred to as the beam of radiation PB, having a desired uniformity and intensity distribution in its cross-section.

The beam of radiation PB is incident on the mask MA, which is held on the mask table MT. Having traversed the mask MA, the beam of radiation PB passes through the lens PL, which focuses the beam onto a target portion C of the substrate W. With the aid of the second positioning device PW and position sensor IF (e.g. an interferometric device), the substrate table WT can be moved accurately, e.g. so as to position different target portions C in the path of the beam PB. Similarly, the first positioning device PM and another position sensor (which is not explicitly depicted in FIG. 1) can be used to accurately position the mask MA with respect to the path of the beam PB, e.g. after mechanical retrieval from a mask library, or during a scan. In general, movement of the object tables MT and WT will be realized with the aid of a long-stroke module (coarse positioning) and a short-stroke module (fine positioning), which form part of the positioning device PM and PW. However, in the case of a stepper (as opposed to a scanner) the mask table MT may be connected to a short stroke actuator only, or may be fixed. Mask MA and substrate W may be aligned using mask alignment marks M1, M2 and substrate alignment marks P1, P2.

The depicted apparatus can be used in the following modes:

Step mode: the mask table MT and the substrate table WT are kept essentially stationary, while an entire pattern imparted to the beam of radiation is projected onto a target portion C at once (i.e. a single static exposure). The substrate table WT is then shifted in the X and/or Y direction so that a different target portion C can be exposed. In step mode, the maximum size of the exposure field limits the size of the target portion C imaged in a single static exposure.

Scan mode: the mask table MT and the substrate table WT are scanned synchronously while a pattern imparted to the beam of radiation is projected onto a target portion C (i.e. a single dynamic exposure). The velocity and direction of the substrate table WT relative to the mask table MT is determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

Another mode: the mask table MT is kept essentially stationary holding a programmable patterning device, and the substrate table WT is moved or scanned while a pattern imparted to the beam of radiation is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above-described modes of use or entirely different modes of use may also be employed.

To show the principle of particle detection by incident radiation and how artifacts may occur, it is illustrated in FIGS. 2-5 how isotropic, i.e. by a particle or other contamination scattered, and non-isotropic, e.g. diffracted or reflected, radiation may be incident on a detector system.

Figure 2:
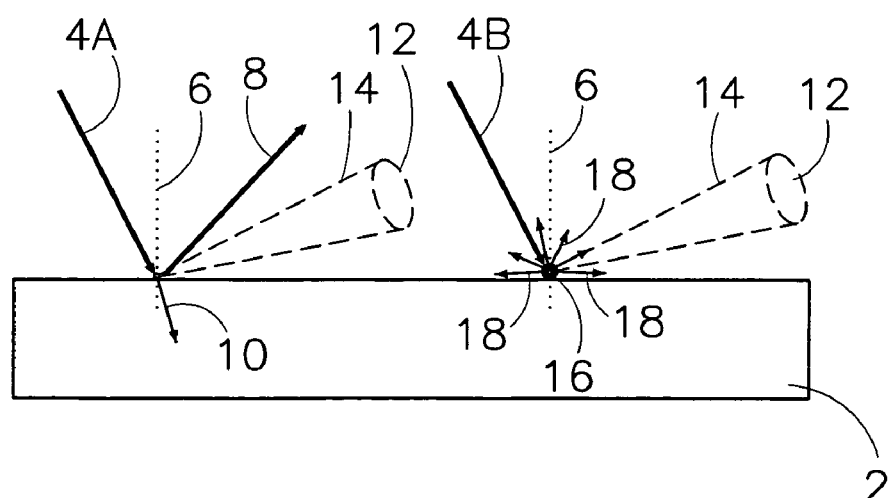
FIG. 2 schematically illustrates redirection of a beam of radiation on an object or on a particle.

FIG. 2 shows an object 2 such as a lithographic mask or substrate. Referring to the left-hand side of FIG. 2, a beam 4A hits the surface of the object 2. At the location where the beam 4A hits the surface, the normal 6, i.e. a line perpendicular to the surface, is indicated. A reflection beam 8 may be reflected according to physical laws known to the person skilled in the art (an exit angle is the same as the angle of incidence with respect to the normal 6). The incident beam 4A may partially be refracted, indicated by a refraction beam 10. Depending on a refraction index of the material of object 2 and on the refraction index of the medium through which the radiation beam 4A travels, the refracted beam 10 is bent towards or away from the normal 6. The amount of radiation being refracted and/or reflected depends on the material of object 2, a surface coating of the object 2 and/or on the angle of incidence, among others.

A detector system 12 detects radiation coming from the location of incidence of the radiation beam 4A, and being directed towards the detector system 12, indicated by a detection cone 14. As is seen from the left-hand side of FIG. 2, an incident beam 4A is anisotropicly reflected as a reflection beam 8 and/or anisotropicly refracted as a refraction beam 10. Thus, in this case, no radiation is incident on the detector and the detector may output a signal having a noise and/or bias level, but not having a significant particle detection level.

Now referring to the right-hand side of FIG. 2, a beam of radiation 4B is incident on a contaminating particle 16 present on the surface of object 2. A part of the incident radiation may be absorbed by the particle 16. Another part may be reflected. Due to the surface shape of the surface of the particle 16, the incident radiation is scattered, i.e. isotropicly reflected. Isotropicly reflected radiation, indicated by arrows 18 is directed in substantially every direction. Therefore, a part of the reflected radiation 18 lies within the detection cone 14 of the detector system 12. Thus, the detector system 12 detects radiation and outputs a signal corresponding to the detected radiation having a level above the particle detection level, i.e. a threshold level.

Figure 3:
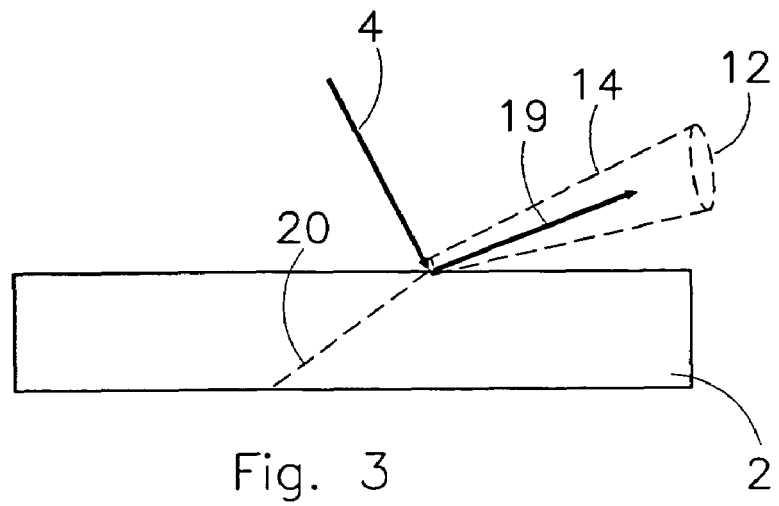
FIG. 3 schematically illustrates a beam of radiation leaving an object being detected by a detector system.

In FIG. 3, an incident beam of radiation 4 is indicated to hit the surface of the object 2. From the location of incidence, a beam of radiation 19 lies within a detection cone 14 of detector system 12 and is incident on the detector system 12. The beam 19 may be radiation having been scattered by a contaminating particle, the detection circuit thus correctly detecting the particle.

However, a beam 20 coming from inside the object 2, as a result of diffraction, refraction and/or reflection as will be explained hereinafter, may leave the object 2 and be refracted such that the beam 19 results. So, if a beam 20 comes from inside the object 2 having such an angle with respect to the normal that its refracted beam 19 lies within the detection cone 14, the detector system 12 detects radiation which was not scattered by a contaminating particle. A detection circuit receiving a signal from the detector system 12 however determines that the signal is above a predetermined threshold level and erroneously indicates that a particle is present. Such a detected, but not actually present particle is herein referred to as a ghost particle.

As will be explained in detail below in relation to FIGS. 4 and 5, an important contributor to the detection of ghost particles is a diffraction pattern. When the object includes a pattern, for example a reflective chrome pattern at a surface, at which surface an entered radiation beam internally diffracts, a diffraction pattern may result. The diffraction pattern may internally reflect and refract and then exit the object such that at least a part of the diffraction pattern will be incident on the detector. Such a diffraction pattern is an anisotropic contribution to the radiation incident on the detector.

A diffraction pattern may include a number of orders, i.e. a zero order pattern, a first order pattern and higher order patterns. A shape, orientation and spacing of the orders of the diffraction pattern is dependent on the shape, orientation and spatial frequency of the diffracting pattern. If a diffracting pattern has a two-dimensional periodic structure, the related diffraction pattern will also be two-dimensional. The energy (intensity) in the diffracted orders depends among others on a duty cycle of the pattern (i.e. a spatial characteristic of the pattern) and on height differences in the pattern. The direction of the diffraction pattern determines whether none, one or more orders of the diffraction pattern may reach the detector system.

A part of a diffraction pattern may be blocked by a diaphragm before the part of the diffraction pattern is incident on the detector. Possibly, another part of the diffraction pattern, such as a second and higher order diffraction pattern may still pass the diaphragm. According to an embodiment of the present invention, the anisotropic radiation will be discriminated from the isotropic radiation, since an isotropic contribution to the radiation will be incident on both parts of the detector despite of the presence of such a diaphragm. Hence, it may be determined whether there is an isotropic contribution to the radiation by verifying that each signal from each part of the detector has a substantially same (if a center of the detector device and the beam of radiation are aligned) level higher than a predetermined threshold or noise level.

The above-described diaphragm splits the detector device in two parts. Despite the presence of the diaphragm, some anisotropic radiation may be incident on the detector device. Moreover, anisotropic radiation may be partly incident on a first part of the detector system and partly incident on a second part of the detector system, thereby generating a substantially same signal level from each detector part. According to a further embodiment of the present invention a second diaphragm prevents such incidence by covering an area between parts of the detector system. Thereto, the width of said diaphragm may be equal to or larger than the expected width of the incident beam of radiation. These embodiments are further elucidated below in relation to FIGS. 6A-6D and 7A-7C.

Figure 4:
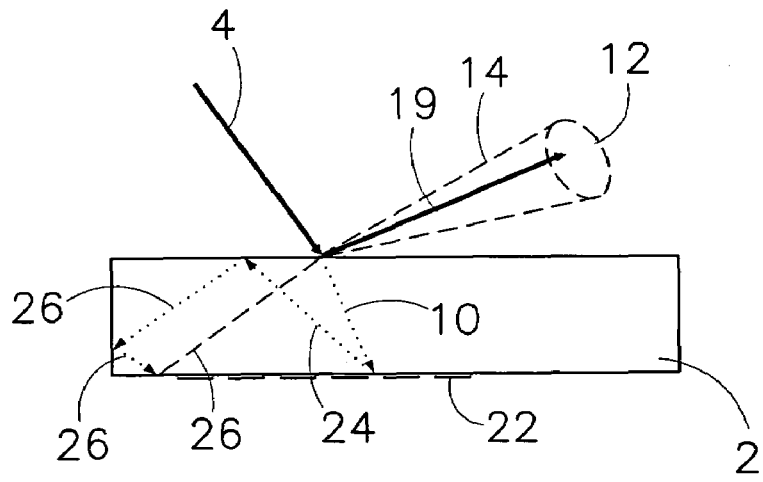
FIG. 4 schematically illustrates how a beam of radiation may internally be refracted, diffracted and/or reflected before leaving the object in the direction of a detector system.

In FIG. 4, it is illustrated how a beam may originate from inside the object 2. The illustrated object 2 is a mask. On one surface, the mask 2 includes a mask pattern 22, which is made, for example, of chromium. An opposite surface of the mask 2 is scanned for particles. There is no particle actually present in the case illustrated in FIG. 4.

A beam 4 is directed at and incident on the surface to be scanned. A part of the incident radiation may be reflected (not shown) and another part may be absorbed and refracted. An absorbed and refracted beam 10 travels through the mask 2. At the opposite surface, the refracted beam 10 hits the mask pattern 22. The mask pattern 22 is a periodic pattern. Due to the periodicity the radiation is diffracted. A diffracted beam 24 travels through the mask 2 and is reflected at the surface of incidence. Subsequent internal reflections at other surfaces may occur, indicated by reflected beams 26. Eventually, an internally reflected beam 26 may approach the location of incidence of the beam 4 such that it leaves the mask 2 and is refracted towards the detector system 12 as indicated by the beam 19. Thus, a ghost particle is detected.

In FIG. 5, again, a refracted beam 19 coming from inside the mask 2 is incident on the detector system 12, but due to another series of reflections, refractions, and/or diffractions compared to the case illustrated in FIG. 4. In the case illustrated in FIG. 5, an incident beam 4 enters the mask 2 and is refracted as refracted beam 10. Given the angle of incidence and the surface conditions, the refracted beam 10 is diffracted or refracted at the opposite surface and leaves the mask 2 as diffracted beam 28. If the diffracted beam 28 is reflected at a surface 32 of another object, such as a pellicle, a reflected beam 26 may hit the surface of the mask 2 again.

The reflected beam 26 is diffracted by periodic mask pattern 22 and enters the mask 2 as a diffracted beam 30. The indicated diffracted beam 30 leaves the mask 2 such that it is refracted towards the detector system 12 and is detected. Similar to FIG. 4, a ghost particle is detected by a detection circuit, although no particle is present.

Figure 5:
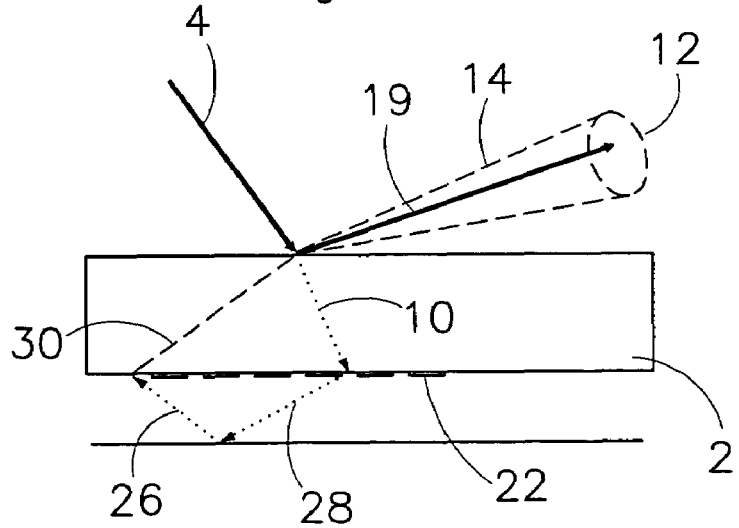
FIG. 5 schematically illustrates how a beam of radiation may internally and externally be refracted, diffracted and/or reflected before leaving the object in the direction of a detector system.

In the above description in relation to FIGS. 3, 4 and 5, it should be noted that reflection, refraction and diffraction are anisotropic. The resulting redirected radiation is included in one or more beams as opposed to scattered, isotropic radiation being redirected in substantially every direction. The multiple diffracted beams are known as (diffraction) orders.

The cross sections of the beams in a diffraction pattern are dependent on the shape of the cross-section of the incident beam of radiation. When, for instance, the incident beam is a single round beam of radiation, the diffraction pattern will be a series of single round beams.

Further, it is noted that FIGS. 2-5 are for illustrative purpose only, since many other light trajectories are possible. For example, although not shown in FIGS. 2-5, radiation coming from other directions than from inside the illustrated cone 14 may be incident on the detector system 12, and thus resulting in the detection of a ghost particle. Other series of reflections, refractions and/or diffractions may result in radiation being directed at the detector system such that a detection of a ghost particle could result.

Figures 6A, 6B, 6C, 6D:
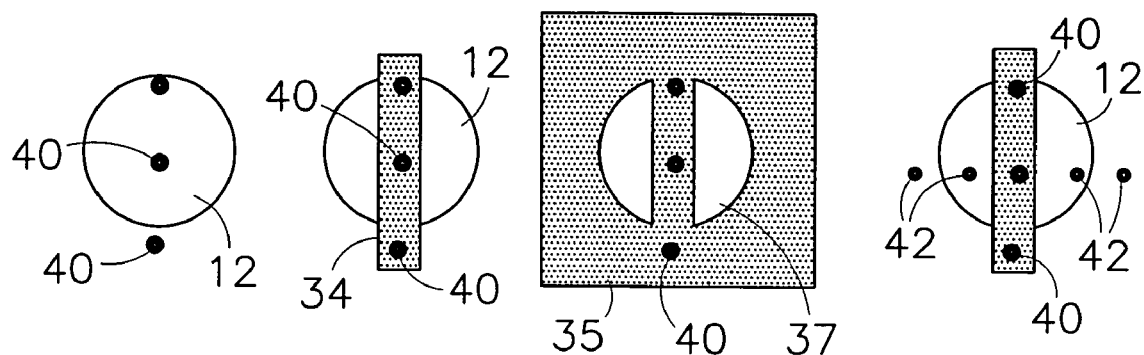
FIGS. 6A-6D schematically illustrate a conventional diaphragm configured to prevent a first order diffraction pattern being incident on the detector system.

In FIG. 6A, a surface of a detector system 12 is indicated. The detector system 12 detects radiation incident on the surface and outputs a corresponding signal. A first diffraction pattern 40 including three spots ($n^{th}$, $(n+1)^{th}$ and $(n+2)^{th}$ order) is partially incident on the detector surface 12. Thus, the detector system 12 detects radiation and outputs a signal corresponding to the intensity of the detected radiation. Since the diffraction pattern 40 is not radiation scattered by a particle, a detection circuit receiving the signal erroneously determines the presence of a particle. To prevent detection of a ghost particle, a diaphragm as shown in FIG. 6B may be used. Such a diaphragm may be positioned between the surface being scanned and the detector.

Now referring to FIG. 6B, a strip-shaped diaphragm 34 may be used to block the first diffraction pattern 40. An isotropic reflection, resulting from scattering by a particle is also partially blocked by the strip-shaped diaphragm 34, however, another part of the isotropic radiation is not blocked and is incident on the detector system 12. Thus, the detector system 12 only detects isotropic scattered radiation and the output signal only results from a present particle.

It is understood that instead of using the strip-shaped diaphragm 34 in front of a detector system 12, a diaphragm 35, as illustrated in FIG. 6C, may be employed similarly. A diaphragm opening 37 lets radiation pass. The strip 34 is positioned in the diaphragm opening 37 and blocks the first diffraction pattern 40.

In FIG. 6D, not only a first diffraction pattern 40 is shown, also a second diffraction pattern 42 including a number of spots is shown. The second diffraction pattern 42 may result from another part of the mask pattern 22 (see FIGS. 4 and 5) or may result from other characteristics of the diffracting pattern. The strip-shaped diaphragm 34 blocks the first diffraction pattern 40, but the second diffraction pattern 42 passes the diaphragm and reaches the detector system 12. Thus, it is still possible that a ghost particle is detected, since a second diffraction pattern 42 may lead to a signal indicating the presence of a particle.

Figures 7A, 7B, 7C:
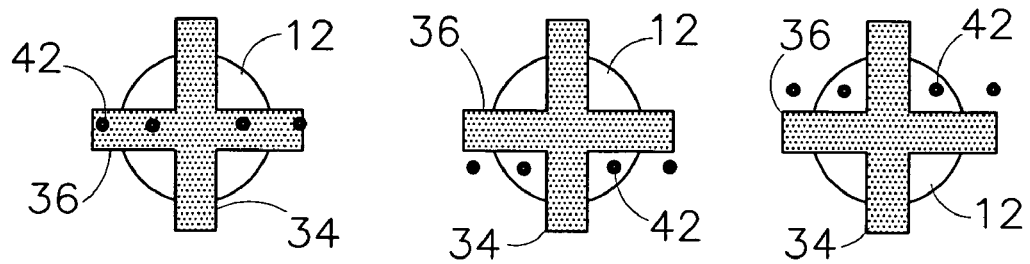
FIGS. 7A-7C schematically illustrate a diaphragm according to an embodiment of the present invention.

In FIGS. 7A-7C, a cross-shaped diaphragm comprising a vertical diaphragm 34 and a horizontal diaphragm 36 is shown. Like in FIG. 6D, the vertical diaphragm 34 blocks the (not shown) first diffraction pattern. The second diffraction pattern 42 may have a number of positions. The width of the diaphragms 34, 36 is selected such that the width is larger than the width of the spots of the diffraction pattern 42.

In FIG. 7A, the second diffraction pattern 42 is blocked by the horizontal diaphragm 36. Thus, no diffracted beam is incident on the detector system 12. In FIG. 7B however, the second diffraction pattern 42 is not blocked, but passes the diaphragm 34, 36, at least partially, and diffracted radiation is incident on the detector system 12. The same applies to the situation shown in FIG. 7C, in which situation the diffraction pattern 42 passes on an opposite side of the horizontal diaphragm 36 compared to the situation illustrated in FIG. 7B.

When the situation shown in FIG. 7A occurs, no ghost particle is detected, since no diffracted radiation is incident on the detector 12. Only isotropic, scattered radiation may be detected. In FIGS. 7B and 7C, the anisotropic diffracted radiation 42 is incident on only one half of the detector system 12: the lower half or the upper half, respectively. Consequently, the other half of the detector system 12 only detects scattered radiation, which is also detected by the other half of the detector system 12 apart from the diffracted radiation. Thus, if two signals corresponding to radiation detected on a corresponding half of the detector system 12, are output by the detector system 12 and diffracted radiation is present, one signal has a higher level than the other due to the contribution of the anisotropic diffracted radiation.

Three situations may occur:

1. Both non-isotropic (diffracted, refracted, reflected) radiation and isotropic (scattered) radiation is incident on the detector system 12;

2. Only isotropic (scattered) radiation is incident on the detector; or

3. Only non-isotropic (diffracted, refracted, and/or reflected) is incident on the detector.

In the first situation, both signals have a level higher than a predetermined noise (threshold) level, indicating that at least isotropic radiation was incident on the detector system 12, and a detection circuit may determine that a particle is present. In the second situation, both halves of the detector output a substantially same signal level, which indicates the presence of only a particle, without a ghost particle contribution. In the third situation, only one of the signals has a level above the noise (threshold) level, indicating that the detected radiation is due to diffraction, refraction and/or reflection, but not to scattering by a particle. A detection circuit may determine that no particle is present.

Another embodiment of the present invention does not depend on spatial discrimination but depends on wavelength related discrimination. As mentioned above, an important contributor to the detection of ghost particles is a diffraction pattern. However, the diffraction patterns are dependent on the wavelength of the incident radiation being diffracted. Using two, or even more radiation sources having each their own specific wavelength, different diffraction patterns are generated. Using a detector for each wavelength, the diffraction pattern for each wavelength is detected by the respective detectors. The choice of wavelength is made such that it is highly improbable that different diffraction patterns, and also other internal reflections and refractions, of the radiation beams of different wavelengths will all reach the corresponding detectors. Thus, similar to the detection method of the above described embodiment, it may be determined whether there is an isotropic contribution to the detected radiation by verifying that each signal from each detector has a level higher than a noise level.

It is noted that the first and second detector may physically be represented by one detector of which the detected signal may be split into a number of contributions coming from the different beams of radiation having different wavelengths. The number of contributions may be determined after simultaneous detection of the number of beams, or the number of contributions may be determined one after another, for example using pulsed radiation sources.

Figure 8:
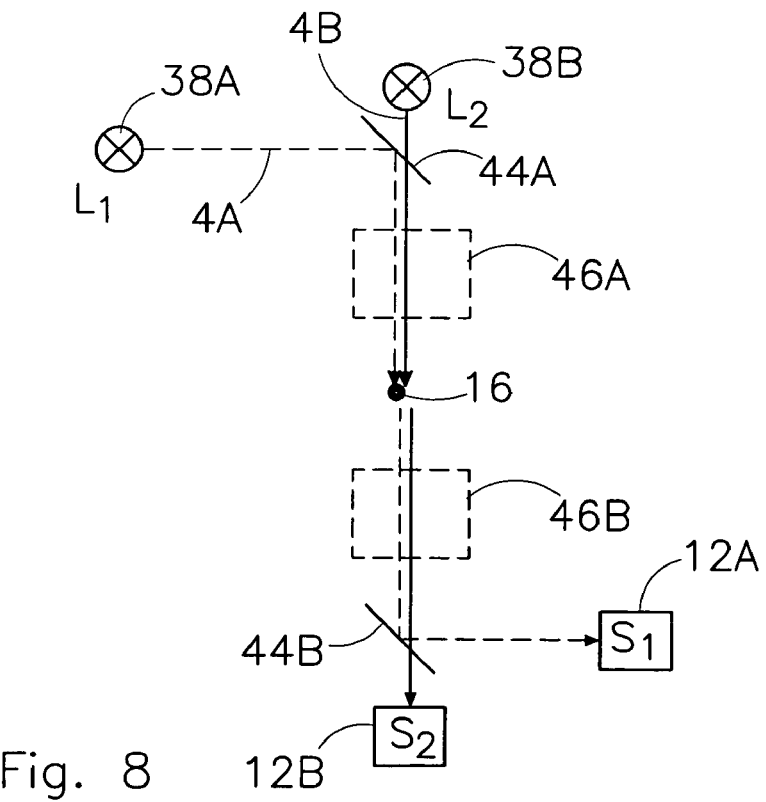
FIG. 8 schematically illustrates a particle detection system including two radiation sources and two radiation detector devices.

FIG. 8 illustrates the above-mentioned embodiment of the present invention, wherein two radiation sources 38A and 38B output two beams of radiation 4A and 4B having different wavelengths. The wavelengths are selected such that it is unlikely that possibly resulting diffraction patterns overlap in their trajectory towards the corresponding detectors. An optical device 44A combines the two radiation beams 4A and 4B and the combined beam is directed at the surface of the object to be scanned. The combined beam may pass through other optical devices 46A and may hit a particle 16, or not.

After being scattered, reflected, refracted and/or diffracted, radiation may travel through a number of optical devices 46B, if present. Then, an optical device 44B splits the radiation into radiation having wavelengths in the range corresponding to beam 4A and radiation having wavelengths in the range corresponding to beam 4B to route the radiation to its corresponding detector 12A or 12B.

The beams 4A and 4B have different wavelengths as mentioned above. Each beam 4 may be a beam of monochrome radiation or including radiation having wavelengths within a certain range of wavelengths. The wavelengths may be different to ascertain that the beams will have different diffraction patterns, since the diffraction patterns are dependent on the wavelength of the incident radiation. When incident radiation beams 4A and 4B enter the object (thus they do not hit a particle), they may be diffracted, reflected and/or refracted such that a part of the incident radiation leaves the object in the direction of a detector 12A or 12B, respectively. Since their diffraction patterns are different due to their different wavelengths, it is virtually impossible that both detectors 12A and 12B receive such anisotropic radiation simultaneously. Thus, if radiation from the beams 4A and/or 4B is diffracted, reflected and/or refracted, only one of the respective detectors 12A and 12B may output a signal having a level above a predetermined threshold level, and therefore it is determined that no particle is present.

When the beams 4A and 4B hit a particle 16, both beams 4A and 4B are being scattered and from both beams 4A and 4B a part of the radiation is scattered/reflected in the direction of their respective detectors 12A and 12B. Thus, when a particle is present, both detectors 12A and 12B receive an amount of radiation and output a signal corresponding to the received amount of radiation having a level above a predetermined noise level, and therefore it is determined that a particle is present. It is noted that, in this embodiment, the first and second detector may physically be represented by one detector of which the detected signal may be split into a number of contributions coming from the different beams of radiation having different wavelengths as mentioned above.

If a particle is present and anisotropicly redirects radiation, and if isotropicly redirected radiation is also incident on one of the detectors, both detectors output a signal having a level above the threshold level. However, one signal has a level representing anisotropicly and isotropicly redirected radiation and another signal has a level representing only anisotropicly redirected radiation. Despite the difference in signal level, the contaminating particle is detected, since both signals have a level above the threshold level, and therefore it is determined that a particle is present. Due to the choice of wavelengths, it is unlikely that both wavelengths will result in an isotropic (ghost) signal in their corresponding detector, and thus reliably discriminating a particle signal from a ghost signal.

Figure 9:
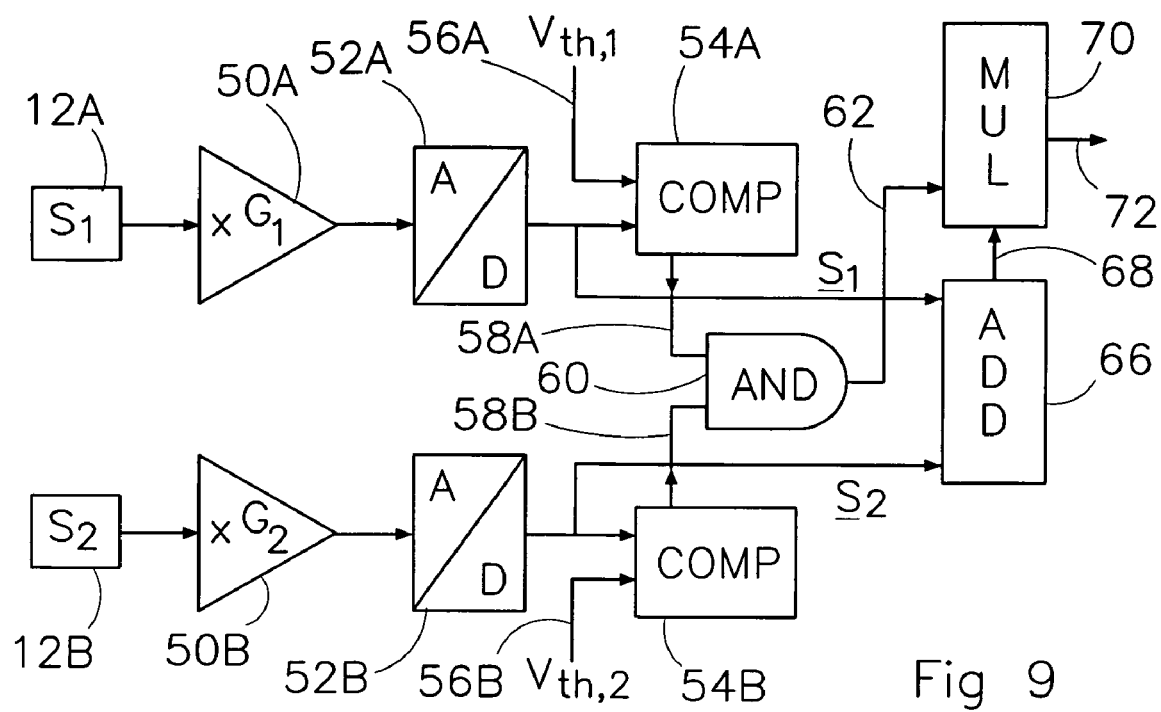
FIG. 9 is a circuit diagram of a detection circuit according to an embodiment of the present invention.

In each of the above-mentioned embodiments of the present invention, two or more independent signals are verified to have a level higher than a threshold level. If all levels are higher than the threshold level, the detector circuit determines that a particle is present on the surface, since it is thus detected that isotropic light is incident on the detector. Therefore, in an embodiment of the present invention as illustrated in FIG. 9, the detection circuit includes a number of comparators configured to compare a corresponding number of input signals with a threshold level, each comparator outputting a logical comparator signal; an AND-operator configured to receive each logical comparator signal and to output a logical TRUE signal when each logical comparator signal represents TRUE. Thus, when a particle is present on the surface, the detection circuit outputs a logical TRUE.

FIG. 9 illustrates a detection circuit for use with the above-described embodiments of the present invention to determine whether a particle is present on a surface, or not. By verifying that a number of signals (in the shown embodiment of the detection circuit two signals) have a level above a threshold level representing a predetermined noise level, it is determined whether a particle is present. The exemplary circuit illustrated in FIG. 9 is a digital circuit. The circuit may however as well be an analogue circuit.

Referring to FIG. 9, a first detector system 12A outputs a signal to an amplifier 50A. The output of the amplifier 50A is input in an analog-to-digital converter 52A. The amplifier 50A is however not an essential component of the detection circuit, since the output of the detector system 12A may be directly input in the analog-to-digital converter 52A. An output of the analog-to-digital converter 52A is fed to a comparator 54A as a first input and a threshold signal 56A representing a predetermined noise level is input in the comparator 54A as a second input. The comparator 54A compares the input signals and outputs a logical comparison signal 58A. The logical comparison signal 58A is input as a first input in an AND-operator 60.

The above described branch of the detection circuit may be present any number of times. In the embodiment shown in FIG. 9, there is a second branch including detector system 12B, amplifier 50B, analog-to-digital converter 52B, comparator 54B, threshold signal 56B and logical comparison signal 58B, which signal 58B is also input in AND-operator 60. Similarly, any number of identical branches may be present in the detection circuit. The AND-operator 60 then has a corresponding number of inputs. A logical AND-operator output 62 represents a logical value indicating whether a particle is present, or not.

The detected amount of scattered radiation is a measure of a size of a detected particle. Therefore, the detection circuit may be adapted not only to indicate whether a particle is present, but also to indicate an estimate of the size of the particle. The logical AND-operator output 62 however only indicates whether a particle is present, since the logical value can only represent 'TRUE' or 'FALSE'. To indicate a size, the signal value of one or both of the detectors should be preserved and presented at an output of the detection circuit, if a particle is detected. The detection circuit shown in FIG. 9 is configured to output the size if a particle is detected, and to output a NULL-signal, if no particle is detected.

Thereto, the detection circuit is provided with an ADD-operator 66, which adds the output of each analog-to-digital converter, in the illustrated embodiment converters 52A and 52B. If more branches are present in the circuit, the ADD-operator 66 has a corresponding number of inputs and adds all input signals. From an output of the ADD-operator 66, an ADD-operator output signal 68 is fed to an MUL-operator 70 multiplying input signals. Beside the ADD-operator output signal 68, the logical AND-operator signal 62 is input in the MUL-operator 70. The MUL-operator output 72 represents the size of a particle if detected, and NULL if no particle is detected, as will be explained below.

A person skilled in the art will from the below description readily understand how the detection circuit functions. It will be appreciated that the circuit may be extended to any number of detector signals. Detectors 12A and 12B output a signal representing the amount of radiation received by the detector system 12A and 12B, respectively. The outputs may be amplified by amplifiers 50A and 50B, respectively, and may be digitized by analog-to-digital converters 52A and 52B, respectively. Alternatively, digital signals S1 and S2 may be processed using an algorithm implemented in software. In software, more complex algorithms may easily be programmed and used, for example. The detection circuit may be analog as well and therefore the converters 52A and 52B may be omitted.

The output of the converters 52A and 52B are thus still representing the signal value of the output of the detectors 12A and 12B, respectively. The output of the converters 52A and 52B are input in the respective comparators 54A and 54B that compare the signal value with a respective threshold value 56A and 56B to determine whether the detector outputs have a level above the threshold. The threshold value 56A, 56B represents a predetermined noise level. If the detector output lies under the noise level, the detector system 12A, 12B did not receive a certain minimum amount of radiation and the output may be assumed to be no more than noise. The comparator 54A, 54B outputs a logical signal 58A, 58B representing 'TRUE' ('1') if the detector output is higher than the threshold value 56A, 56B, and representing 'FALSE' ('0') if the detector output is lower than the threshold value 56A, 56B.

If both comparators 54A and 54B output a logical TRUE ('1'), the AND-operator 60 receives only signals 58A, 58B representing TRUE and therefore outputs a logical TRUE ('1'). If one or none of the inputs 58A, 58B represents FALSE ('0'), the output 62 of the AND-operator 60 represents FALSE ('0').

The ADD-operator 66 adds the detector outputs independent from whether a particle is detected, or not. Adding the detector outputs is particularly suited for the embodiment described in relation to the embodiment of FIG. 7, since in that embodiment the received amount of radiation is divided over two halves of the detector and is output as two separate signals. The two separate signals added together then represents the total received amount of radiation. The two detectors 12A and 12B shown in FIG. 9 should in that case be interpreted as two halves of one detector. Thus, the ADD-operator output signal 68 represents a total received amount of radiation.

In an embodiment of the invention, the detection circuit may be configured to determine a size of a detected particle based on the detector signal. The level of the detector signal represents an intensity of the detected radiation incident on the detector. The intensity of the incident radiation is a measure for the size of the detected particle.

The ADD-operator output signal 68 is input in the MUL-operator 70. The MUL-operator 70 further receives a logical TRUE ('1') or FALSE ('0') when a particle is present and when a particle is not present, respectively. Thus, when a particle is present, the MUL-operator 70 multiplies the ADD-operator output signal 68 and the logical TRUE ('1') resulting in an output signal 72 having the same signal value as the ADD-operator output signal 68. The ADD-operator output signal 68 represents the amount of radiation received by the detectors 12A and 12B, and thus is a measure of the size of a detected particle. The output 72 of the MUL-operator 70 therefore represents the size of a detected particle, since, if no particle is detected, the ADD-operator output signal 68 is multiplied by 0 ('FALSE') and would represent NULL.

When receiving more than one signal, one from each part of a detector as described above in relation to one or more embodiments of the present invention, or one or more signals from more than one detector, each separate signal or a combination of two or more signals may be used to determine the particle size. A suitable combination may be, for example, the sum of two signals coming from one detector, thus reconstructing the intensity of radiation incident on the whole detector.

Light incident on a detector may include both isotropically and anisotropically redirected light, i.e. light redirected by a particle and light representing a ghost particle. Thus, both signals may have a level higher than the threshold level, while a first signal may have a substantially higher level than a second signal. In such a case, the first signal is generated due to both the isotropic contribution and the anisotropic contribution to the incident light. The second signal only represents the isotropic contribution, i.e. the radiation resulting from scattering by a particle. Therefore, in an embodiment of the detection circuit, the signal having the lowest level may be used for determining the particle size.

Instead of using the ADD-operator 66, it will be appreciated that any other circuitry may be employed to output a signal representing a size of a particle. For example, it may be considered that if both detectors 12A and 12B output a high signal, one of them may have received not only scattered isotropic radiation, but also non-isotropic radiation. Therefore, one signal may be substantially higher than the other. In such a case, it is considered to use only the lower signal, since it is assumed that the lower signal represents only scattered radiation and may thus be more representative for the size of the scattering particle. A person skilled in the art readily understands how a circuit may be built using logical operators or analogue circuitry, which circuit selects the lower signal and outputs the signal to the MUL-operator 70 shown in FIG. 9.

In order to detect reticle contamination and to measure size of contaminant particles, internal or external reticle inspection systems may be used. These systems may contain a digital camera or a scanner to obtain a two-dimensional image of (or part of) the surface of the reticle.

Estimating the size of particles which are smaller than the resolution (pixel size or spot size of the scanning beam) of the two-dimensional imaging system can be done by measuring the maximum reflected signal intensity (pixel intensity) when the particle is exposed with light and by comparing it with the amount of light reflected by standard latex spheres of known dimensions.

It is also possible to extract particle features from the two-dimensional bitmap, like shape and size. These two-dimensional bitmaps can be used to estimate the size of particles that are larger than the resolution of the two-dimensional imaging system. This method can be referred to as Image feature method. This method is generally accurate only for particles that are significantly larger than the resolution of the two-dimensional imaging system. In a practical embodiment, the latter may be about 70 μm.

Although the latex equivalent sphere (LES) reflection method works well for contaminant particles that are smaller than the resolution of the two-dimensional imaging system, this method may not be desirable for larger particles because it may result in unrealistic estimates, basically classifying those particles as being too small. The range of latex spheres used in the reflection method is generally limited to from 10 to 100 μm.

Since particles are detected on the top surface of the reticle and/or on the bottom surface of the pellicle (hard or soft), particles may always be at an out-of-focus position with respect to the pattern on the reticle, which implies that small particles are not as relevant as large particles since they have less impact on imaging. Therefore, the contamination detection method of choice should also correctly estimate the size of particles larger than about 60 μm.

In an embodiment of the invention, a new method for detecting particles on an object is presented. First, a two-dimensional image of the reticle is obtained. This two-dimensional image contains particle reflection intensities. Then, individual particles are located by scanning this image for clusters of connected pixels with an intensity above a certain threshold. The size of each pixel cluster may be determined according to the image feature method but if this size is less than a predefined value, then the latex equivalent sphere reflection method may be used instead. The particle size according to the image feature method is extracted from the image by determining, in an embodiment of the invention, the width and height of a rectangular bounding box including all cluster pixels. Alternatively, the number of cluster pixels, the diagonal of the bounding box, or the maximum distance between 2 cluster pixels can be used, for example. It will be appreciated that a particle may be strongly asymmetric (e.g. the width of the bounding box is much larger than its height) in which case the image feature method may be used.

It will be appreciated that the resulting method may be capable of detecting both small and large particles, where the range is in practice only limited by the size of the two-dimensional image.

Another embodiment of the present invention depends on spatial discrimination on the surface of the detector device. Referring to FIGS. 10A and 10B, illustrating this embodiment of the present invention, a radiation blocking assembly 130 is positioned in a radiation trajectory 120 (optical axis) from the surface 102A of an object 102 to a radiation detector device 112. The radiation blocking assembly 130 comprises a lens 131 and a diaphragm 132. A contaminating particle 116 is present on the surface 102A of the object 102. A beam of radiation 110 is incident on the particle 116. A resulting scattered beam of radiation redirected by the particle 116 is shown as cone 114 propagating towards the detector device 112.

The lens 131 is configured to focus radiation coming from a radiation source in a plane of the surface 102A of the object 102 in a plane of the detector device 112. Thus, the beam of radiation 114 scattered by the particle 116 is focused onto the detector device 112. The diaphragm 132, however, blocks a part of the radiation incident on the lens 131. A part of the radiation of cone 114 passes the diaphragm 132 and is still being focused on detector device 112. An effect resulting from the diaphragm 132 for the image of the contaminating particle 116 is a loss of radiation intensity on the detector device 112.

Now referring to FIGS. 10C and 10D, further illustrating the above-mentioned embodiment, the diaphragm 132 is positioned in a radiation trajectory 120 (optical axis) from the surface 102A of an object 102 to the radiation detector device 112.

In FIGS. 10C and 10D, no contaminating particle is present on the surface 102A of the object 102. A beam of radiation (not shown) is incident on the surface 102A. The beam has been refracted into the object 102 and is in the object 102 reflected and possibly diffracted at a pattern surface 102B. A resulting beam of diffracted radiation inside cone 118 is shown as beam 119. The cone 118 may be regarded as an assembly of possible anisotropic beams of radiation coming from a ghost particle 122 and directed toward lens 131.

The diaphragm 132 blocks a part of the isotropic radiation directed toward the lens 131. The part of the radiation of cone 114 passing the diaphragm 132 is being focused on the detector device 112. The effect resulting from the diaphragm 132 for the image of the particle 116A is a loss of radiation intensity on the detector device 112.

When an anisotropic beam is generated in the pattern surface 102B then the point where this beam leaves surface 102B can be regarded as the location of a ghost particle 122. Due to refraction at surface 102A the ghost beam will have a different direction when it leaves object 102, and it will seam that the ghost beam has its origin in the virtual ghost particle 122A as drawn in FIG. 10C. If the beam reaches lens 131 it will be located inside cone 118. Regarding an anisotropic beam coming from the ghost particle 122 inside cone 118 there are two possibilities: either the beam is blocked by diaphragm 132 or the beam (partly) passes diaphragm 132, is incident on the lens 131 and is focused in point 117. Point 117 is the image of ghost particle 122 made by lens 131. Because ghost particle 122A is located further away from lens 131 than particle 116, the image in point 117 is located at some distance in front of the image of particle 116 on the detector device 112 according to the laws of optical imaging. After passing the point 117 the radiation from ghost particle 122 propagates further towards the detector device 112 and results in a spot in area 112B or 112C of detector device 112, outside area 112A.

In FIG. 10E the areas 112A, 112B and 112C are depicted on a larger drawing scale. Area 112A can be described as a shadow of diaphragm 132 made by all possible beams in cone 118 that come from particle 122, focused in point 117. Hence, no radiation resulting from a ghost particle 122 is present in a part 112A of the detector device 112. The part 112A of the detector device 112 may be referred to hereinafter as a no-ghost detection part 112A of the detector device 112. Therefore in the situation drawn in FIG. 10A to 10D signals from area 112A are only related to particle 116 and not to ghost particle 122.

However, in exceptional cases, through double diffraction on two-dimensional patterns, a ghost particle may appear to lie out of the plane of drawing 10C; in such a case a ghost particle may enter area 112A, and 112B or 112C. To prevent an incorrect determination of the presence of a particle, in an embodiment, signals from area 112B or 112C related to ghost particle 122 may be employed. An image 133 of particle 116 on detector device 112 (FIG. 10E) is within area 112A. Therefore, signals from area 112B or 112C are only related to a ghost particle 122 and not to an actual particle 116. Signals from area 112B or 112C can be used to warn for the presence of a ghost particle 122. This is useful for the above-described situation of a ghost particle located out of the plane of drawing 10C where a signal from area 112A could be misinterpreted as a signal from a particle 116 while the signal actually is related to a ghost particle. Thus, the signals from area 112B or 112C enable to correct a misinterpretation.

The size of the no-ghost detection part 112A is dependent on the distance of the ghost particle 122 and a focal point of the lens 131. The focal point of the lens 131 is selected such that the radiation scattered by a contaminating particle 116 is focused on a part 112A of the detector device 112. The size of the no-ghost detection part 112A depends, inter alia, on the focal point of the lens 131, a distance between the detector device 112 and the point 117 and a size of the diaphragm 132.

It is noted that a person skilled in the art may combine the embodiment as illustrated in FIGS. 10A to 10E, and described above, with the embodiment as described in relation to FIGS. 6-9 without using any inventive skills. For example, the diaphragm 132 may have a shape as shown in FIG. 6A-6D or FIG. 7A-7C. In such an embodiment, a width of the diaphragm 132 may be, in side view and/or in top view, substantially equal to a width of the lens 131.

While the invention has been described and illustrated in its preferred embodiments, it should be understood that departures may be made therefrom within the scope of the invention, which is not limited to the details disclosed herein.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention.

The terms "a" or "an," as used herein, are defined as one or more than one. The term "plurality," as used herein, is defined as two or more than two. The term another, as used herein, is defined as at least a second or more. The terms "including" and/or "having," as used herein, are defined as comprising (i.e., open language). The term "coupled," as used herein, is defined as connected, although not necessarily directly, and not necessarily mechanically.

What is claimed is:

1. A particle detection system configured to detect a particle on a surface of an object, the system comprising:
   a first radiation source configured to generate a beam of radiation having a first wavelength, the beam of radiation being directed to a detection area at the surface of the object;
   a radiation detector system configured to output a plurality of detector signals corresponding to an intensity of radiation received from the detection area incident on the radiation detector system; and
   a detection circuit coupled to the radiation detector system and configured to determine from the plurality of detector signals whether a particle is present on the surface of the object,
   wherein presence of a particle is determined by resolving a substantially anisotropic signal from a ghost particle relative to a substantially isotropic signal from the particle.

2. The particle detection system of claim 1, wherein the detection circuit is configured to compare each of the plurality of detector signals with a predetermined threshold level, and to indicate that a particle is present on the surface of the object, when each of said plurality of detector signals has a level above said threshold level.

3. The particle detection system of claim 2, further comprising a cross-shaped diaphragm positioned between the surface of the object and the radiation detector system, wherein the radiation detector system comprises a detector device, said detector system being configured to output a first detector signal corresponding to the intensity of radiation incident on a first part of the detector system, and to output a second detector signal corresponding to the intensity of radiation incident on a second part of the detector system.

4. The particle detection system of claim 2, further comprising a second radiation source configured to generate a beam of radiation having a second wavelength, the beam of radiation being directed to the surface of the object, wherein the detector system comprises a first detector device configured to output a first detector signal corresponding to an intensity of radiation having the first wavelength and being incident on the first detector, and a second detector device configured to output a second detector signal corresponding to an intensity of radiation having the second wavelength and being incident on the second detector device.

5. The particle detection system of claim 2, wherein the detector system comprises (1) a first detector subsystem, the first detector subsystem being configured to output a first detector signal corresponding to the intensity of radiation incident on a first part of the first detector subsystem, and to output a second detector signal corresponding to the intensity of radiation incident on a second part of the first detector subsystem, and (2) a second detector subsystem, the second detector subsystem being configured to output a third detector signal corresponding to the intensity of radiation incident on a first part of the second detector subsystem, and to output a fourth detector signal corresponding to the intensity of radiation incident on a second part of the second detector subsystem; and wherein the system further comprises a cross-shaped diaphragm positioned between the surface of the object and each detector.

6. The particle detection system of claim 2, wherein the detection circuit comprises a plurality of comparators configured to compare a corresponding plurality of input detector signals with a threshold level, each of the plurality of comparators outputting a logical comparator signal, and an AND-operator configured to receive each logical comparator signal and to output a logical TRUE signal when each of the plurality of input signals is greater than the threshold level.

7. The particle detection system of claim 2, wherein the detection circuit is further configured to determine a size of a detected particle based on the detector signal.

8. The particle detection system of claim 7, wherein the size of the detected particle is determined based on one detector signal or a combination of at least two detector signals.

9. The particle detection system of claim 7, wherein the radiation detector system comprises a detector device comprising an array of detector pixel elements, each detector signal of the plurality of detector signals corresponding to an intensity of radiation incident on at least one detector pixel element, thereby providing a particle image of a detected particle, the image comprising a number of image pixels, wherein the detection circuit is configured to
   detect whether a detected particle is small or large based on the particle image;
   determine the size of a small particle based on the radiation intensity incident on at least one detector pixel element; and
   determine the size of a large particle based on image features of the particle image.

10. The particle detection system of claim 9, wherein the detection circuit is configured to detect that a particle is small if a total number of image pixels relating to the detected particle is smaller than a predetermined number of pixels.

11. The particle detection system of claim 4, wherein a size of the particle is determined based on the signal from the first detector, the signal from the second detector or a combination of the signals from the first and the second detector.

12. The particle detection system of claim 1, wherein the radiation detector system comprises a radiation detector device for generating the first detector signal in response to radiation incident on at least one predetermined part of the radiation detector device; and
  a radiation blocking assembly for preventing radiation not originating from the detection area around the surface of the object from being incident on the predetermined part of the radiation detector device.

13. The particle detection system of claim 12, wherein the radiation blocking assembly comprises:
  a detector lens for focusing radiation originating from the detection area on the at least one predetermined part of the radiation detector device;
  a blocking device for preventing radiation not originating from the detection area from being directed by the detector lens onto the predetermined part of the detector device.

14. The particle detection system of claim 12, wherein the radiation detector system is configured to further output at least a second detector signal for indicating whether radiation is incident on the radiation detector device outside said at least one predetermined part of the radiation detector device for detecting a ghost particle signal.

15. The particle detection system of claim 12, wherein the detection circuit is further configured to determine a size of a detected particle based on the detector signal.

16. The particle detection system of claim 15, wherein the detector system comprises a detector device comprising an array of detector pixel elements, each detector signal of the plurality of detector signals corresponding to an intensity of radiation incident on at least one of said detector pixel elements, the plurality of detector signals thereby providing a particle image of a detected particle, the image comprising a number of image pixels, wherein the detection circuit is configured to
  detect whether a detected particle is small or large based on the particle image;
  determine the size of a small particle based on the radiation intensity incident on at least one detector pixel element; and
  determine the size of a large particle based on image features of the particle image.

17. The particle detection system of claim 16, wherein the detection circuit is configured to detect that a particle is small if a total number of image pixels relating to the detected particle is smaller than a predetermined number of pixels.

18. A lithographic apparatus comprising:
  an illumination system configured to condition a beam of radiation;
  a support structure configured to support a patterning device, the patterning device serving to impart the beam of radiation with a pattern in its cross-section;
  a substrate table configured to hold a substrate;
  a projection system configured to project the patterned beam onto a target portion of the substrate, and
  a particle detection system configured to detect a particle in a detection area at a surface of an object, wherein presence of a particle is determined by spatially resolving in a radiation beam received from the detection area a signal from a ghost particle from a signal from the particle.

19. The lithographic apparatus of claim 18, wherein said particle detection system comprises a detection circuit configured to compare a plurality of detector signals with a predetermined threshold level, and to indicate that a particle is present on the surface of the object, when said plurality of detector signals has a level above said threshold level.

20. The lithographic apparatus of claim 19, the particle detection system further comprising a cross-shaped diaphragm positioned between the surface of the object and the detector system, wherein the radiation detector system comprises a detector, said detector being configured to output a first detector signal corresponding to the intensity of radiation incident on a first part of the detector, and to output a second detector signal corresponding to the intensity of radiation incident on a second part of the detector.

21. The lithographic apparatus of claim 19, the particle detection system further comprising a second radiation source configured to generate a beam of radiation having a second wavelength, the beam of radiation being directed to the surface of the object, wherein the detector system comprises a first detector configured to output a first detector signal corresponding to an intensity of radiation having the first wavelength and being incident on the first detector, and a second detector configured to output a second detector signal corresponding to an intensity of radiation having the second wavelength and being incident on the second detector.

22. The lithographic apparatus of claim 19, wherein the detector system of the particle detection system comprises a first detector, the first detector being configured to output a first detector signal corresponding to the intensity of radiation incident on a first part of the first detector, and to output a second detector signal corresponding to the intensity of radiation incident on a second part of the first detector, and a second detector, the second detector being configured to output a third detector signal corresponding to the intensity of radiation incident on a first part of the second detector, and to output a fourth detector signal corresponding to the intensity of radiation incident on a second part of the second detector; and wherein the system further comprises a cross-shaped diaphragm positioned between the surface of the object and each detector.

23. The lithographic apparatus of claim 19, wherein the detection circuit of the particle detection system comprises a plurality of comparators configured to compare a corresponding plurality of input detector signals with a threshold level, each of the plurality of comparators outputting a logical comparator signal, and an AND-operator configured to receive each logical comparator signal and to output a logical TRUE signal when each of the plurality of input signals is greater than the threshold level.

24. The lithographic apparatus of claim 18, wherein the detection circuit is further configured to determine a size of a detected particle based on the detector signal.

25. The lithographic apparatus of claim 24, wherein the size of the detected particle is determined based on one detector signal or a combination of at least two detector signals.

26. The lithographic apparatus of claim 24, wherein the detector system comprises a detector device comprising an array of detector pixel elements, each detector signal of the plurality of detector signals corresponding to an intensity of radiation incident on at least one detector pixel element, thereby providing a particle image of a detected particle, the image comprising a number of image pixels, wherein the detection circuit is configured to:
  detect whether a detected particle is small or large based on the particle image;
  determine the size of a small particle based on the radiation intensity incident on at least one detector pixel element; and determine the size of a large particle based on image features of the particle image.

27. The lithographic apparatus of claim 26, wherein the detection circuit is configured to detect that a particle is small if a total number of image pixels relating to the detected particle is smaller than a predetermined number of pixels.

28. The lithographic apparatus of claim 21, wherein a size of the particle is determined based on the signal from the first detector, the signal from the second detector or a combination of the signals from the first and the second detector.

29. The lithographic apparatus of claim 18, wherein said object is the substrate or the patterning device.

30. The lithographic apparatus of claim 18, the particle detection system comprising:
    a radiation detector device for generating a first detector signal in response to radiation incident on at least one predetermined part of the radiation detector device; and
    a radiation blocking assembly for preventing radiation not originating from the detection area around the surface of the object from being incident on the predetermined part of the radiation detector device.

31. The particle detection system of claim 30, wherein the radiation blocking assembly comprises:
    a detector lens for focusing radiation originating from the detection area on the at least one predetermined part of the radiation detector device;
    a blocking device for preventing radiation not originating from the detection area from being directed by the detector lens onto the predetermined part of the detector device.

32. The particle detection system of claim 31, wherein the radiation detector system is configured to further output at least a second detector signal for indicating whether radiation is incident on the detector device outside said at least one predetermined part of the detector device for detecting a ghost particle signal.

33. A device manufacturing method comprising:
    projecting a patterned beam of radiation onto a target portion of a substrate, and
    detecting a particle on a surface of an object, said detecting including:
    providing a beam of radiation onto the surface of said object,
    detecting the beam of radiation redirected by said particle and/or said object;
    directing a beam of radiation originating from within a detection range around the surface of the object on a predetermined part of a radiation detection device;
    preventing radiation not originating from within the detection range around the surface of the object from being incident on the predetermined part of the radiation detection device; and
    detecting the presence of a particle on the surface of said object based on a detector signal corresponding to an intensity of the detected beam of radiation incident on the predetermined part of the radiation detection device.

34. The particle detection system of claim 1, wherein the presence of a particle is determined by spatially resolving the substantially anisotropic signal from a ghost particle relative to the substantially isotropic signal from the particle.

35. The particle detection system of claim 1, wherein the substantially anisotropic signal from a ghost particle is resolved relative to the substantially isotropic signal from the particle using at least two radiation wavelengths.

* * * * *